US009320464B2

(12) United States Patent
Volmer et al.

(10) Patent No.: US 9,320,464 B2
(45) Date of Patent: Apr. 26, 2016

(54) METHOD AND MEASURING INSTRUMENT FOR MEASURING THE OXYGEN SATURATION IN THE BLOOD

(75) Inventors: Achim Volmer, Lübeck (DE); Reinhold Orglmeister, Berlin (DE); Eugen Hoffmann, Berlin (DE); Dorothea Kolossa, Witten (DE)

(73) Assignee: Technische Universitat Berlin, Berlin (DE)

( * ) Notice: Subject to any disclaimer, the term of this patent is extended or adjusted under 35 U.S.C. 154(b) by 826 days.

(21) Appl. No.: 13/576,389

(22) PCT Filed: Jan. 28, 2011

(86) PCT No.: PCT/DE2011/050002
§ 371 (c)(1),
(2), (4) Date: Jul. 31, 2012

(87) PCT Pub. No.: WO2011/095162
PCT Pub. Date: Aug. 11, 2011

(65) Prior Publication Data
US 2012/0302846 A1 Nov. 29, 2012

(30) Foreign Application Priority Data
Feb. 2, 2010 (DE) .......................... 10 2010 006 956

(51) Int. Cl.
*A61B 5/1455* (2006.01)
*A61B 5/024* (2006.01)
(Continued)

(52) U.S. Cl.
CPC ......... *A61B 5/14551* (2013.01); *A61B 5/02416* (2013.01); *A61B 5/7214* (2013.01); *G06K 9/624* (2013.01)

(58) Field of Classification Search
CPC . A61B 5/14551; A61B 5/7207; A61B 5/7239
See application file for complete search history.

(56) References Cited

U.S. PATENT DOCUMENTS

| 5,706,402 A | 1/1998 | Bell |
| 5,922,607 A | 7/1999 | Bernreuter |

(Continued)

FOREIGN PATENT DOCUMENTS

| DE | 196 51 690 A1 | 6/1997 |
| DE | 102004 16 435 B4 | 5/2009 |
| EP | 0 555 553 A2 | 8/1993 |

OTHER PUBLICATIONS

Baumann, Wolf, "Optimierung frequenzvarianter Nullbeamformer für akustische Signale mittels Statistik höherer Ordnung—Anwendungen im Kfz und in Büroräumen [Optimizing frequency-variant zero-beam former for acoustic signals by means of higher-order statistics—applications in motor vehicles and office space]," Berlin 2005, pp. i-xii and 1-131.

(Continued)

*Primary Examiner* — Eric Winakur
(74) *Attorney, Agent, or Firm* — Gordon & Rees LLP (57) ABSTRACT

The invention relates inter alia to a method for measuring the oxygen saturation of the blood flowing in a peripheral human or animal body part (20), in which electromagnetic radiation ($q1'(t)$, $q2'(t)$) having a first and a second wavelength is irradiated into the peripheral body part or irradiated through the peripheral body part, the reflected or transmitted radiation ($x1'(t)$, $x2'(t)$) is measured to form two measurement signals ($x1(t)$, $x2(t)$), and the oxygen saturation of the blood is determined by evaluating the two measurement signals. According to the invention, provision is made for a mathematical mixing model to be used to evaluate the two measurement signals and a statistical evaluation method to be applied to the two measurement signals, wherein, as a boundary condition, the statistical independence of a useful source signal and an interference source signal is assumed and the useful source signal and the two useful-signal-related filter functions are determined with the aid of the evaluation method and the oxygen saturation of the blood is determined using the three aforementioned signals.

8 Claims, 3 Drawing Sheets

(51) Int. Cl.
*A61B 5/00* (2006.01)
*G06K 9/62* (2006.01)

(56) References Cited

U.S. PATENT DOCUMENTS

| | | | |
|---|---|---|---|
| 2003/0088164 | A1 | 5/2003 | Stetson |
| 2004/0267140 | A1 | 12/2004 | Ito et al. |
| 2005/0058456 | A1 | 3/2005 | Yoo |
| 2006/0009688 | A1 | 1/2006 | Lamego et al. |
| 2006/0111623 | A1 | 5/2006 | Stetson |
| 2006/0189882 | A1 | 8/2006 | Thomas |
| 2007/0219439 | A1 | 9/2007 | Vilser et al. |
| 2007/0257840 | A1 | 11/2007 | Wang et al. |
| 2008/0045823 | A1 | 2/2008 | Diab et al. |

OTHER PUBLICATIONS

Belouchrani, Adel et al., "A Blind Source Separation Technique Using Second-Order Statistics," IEEE Transactions on Signal Processing, Feb. 1997, vol. 45, No. 2, pp. 434-444.

Bronzino, Joseph D., ed., "The Biomedical Engineering Handbook," CRC Press LLC, 2000, Second Edition, vol. 1, 32 pages.

Delfosse, Nathalie et al., "Adaptive Blind Separation of Independent Sources: A Second-Order Stable Algorithm for the General Case," IEEE Transactions on Circuits and Systems Part I: Regular Papers, IEEE Service Center, New York, NY, Jul. 1, 2000, vol. 47, No. 7.

Hyvärinen, Aapo et al., "Independent Component Analysis," John Wiley & Sons, Inc., 2001, 18 pages.

International Search Report in corresponding PCT Application No. PCT/DE2011/050002 dated Jun. 29, 2011.

Jensen, T. et al. "Independent Component Analysis Applied to Pulse Oximetry in the Estimation of the Arterial Oxygen Saturation (Sp02)—A Comparative Study," 2009 Annual International Conference of the IEEE Engineering in Medicine and Biology Society: EMBC 2009, Minneapolis, Minnesota, Sep. 3-6, 2009, pp. 4039-4044.

Kohler, Bert-Uwe, "Konzepte der statistischen Signalverarbeitung [Concepts of Statistical Signal Processing]," Springer Berlin Heidelberg New York, 2005, 9 pages.

Oppenheim, Alan V. et al., "Zeitdiskrete Signalverarbeitung [Time-discrete signal processing]," Pearson Studium, 2004, 10 pages.

Parra, L. C. "An Introduction to Independent Component Analysis and Blind Source Separation," Internet Citation, Apr. 25, 1999.

Proakis, John G. et al., "Digital Signal Processing—Principles, Algorithms and Applications," Pearson Education, 2007, http://www.amazon.co.uk/gp/product/toc/0131873741/ref=dp_toc/276-1109979-2388 . . . , printed May 16, 2012, 4 pages.

Rahbar, Kamran and James P. Reilly, "A Frequency Domain Method for Blind Source Separation of Convolutive Audio Mixtures," IEEE Transactions on Speech and Audio Processing, Sep. 2005, vol. 13, No. 5, pp. 832-844.

METHOD AND MEASURING INSTRUMENT FOR MEASURING THE OXYGEN SATURATION IN THE BLOOD

RELATED APPLICATIONS

This application is a U.S. National Phase of PCT/DE2011/050002, filed Jan. 28, 2011, which claims priority from German Patent Application No. 10 2010 006 956.6, filed Feb. 2, 2010, both of which are hereby incorporated by reference in their entireties.

The invention relates to a method having the features as per the preamble of patent claim 1.

Such a method is described in the document [Bro00]. In this method, the oxygen saturation of the blood flowing in a peripheral human or animal body part is measured by virtue of irradiating electromagnetic radiation having a first and a second wavelength through the peripheral body part, the transmitted radiation being measured to form two measurement signals and the oxygen saturation of the blood being determined by evaluating the two measurement signals.

Further methods for measuring the oxygen saturation are described in documents US 2006/0009688 A1, DE 10 2004 016 435 B4, DE 196 51 690 and EP 555 553 A2.

It is well-known that pulse oximetry allows the non-invasive, continuous measurement of the oxygen saturation of the arterial blood. This is a spectral photometric method based on the different light absorption of oxygenated and deoxygenated hemoglobin. Moreover, the pulsating flow of the blood and the change in the arterial diameter connected therewith are utilized, as a result of which it is also possible to establish the heart rate in addition to determining the oxygen saturation.

In the body, 98% of the oxygen transport is performed by the hemoglobin. Only approximately 1-2% of the oxygen is dissolved in the plasma. Hemoglobin is predominantly present in the blood in four fractions. In addition to the reduced and oxygenated hemoglobin, which are responsible for transporting oxygen, dyshemoglobins, such as carboxyhemoglobin and methemoglobin, are also present. The oxygen saturation represents the concentration ratio between oxygenated and deoxygenated hemoglobin.

All fractions of hemoglobin have different absorption spectra, which are utilized in pulse oximetry.

In the case of a transmissive measurement, a peripheral body part, generally a finger, toe or earlobe, is illuminated from one side using light with a specific wavelength and the transmitted light is detected on the other side.

The theoretic basis is formed by the Beer-Lambert law, which describes the intensity attenuation of light of one wavelength when passing through an absorbing substance. This attenuation is determined by the thickness, the concentration and the absorption coefficient, which depends on the respective wavelengths. If monochromatic light is irradiated into a medium, one part is absorbed while the other part is transmitted. In the process, the intensity is attenuated exponentially with respect to the thickness of the irradiated medium.

Blood is only transparent in the optical window between 600 nm and 1300 nm. Below 600 nm, the melanin of the red blood cells absorbs the light too strongly; above 1300 nm, the tissue fluid absorbs the light too strongly. The wavelength range that can be used for a measurement is restricted accordingly.

In the case of conventional pulse oximeters, one restricts oneself to determining the functional oxygen saturation. To this end, it is necessary to establish the concentrations of oxygenated and reduced hemoglobin. A light source at 660 nm, i.e. in the red region, and an infrared source at 940 nm are conventional.

The absorption is composed of a constant and a pulsating component. The constant component emerges from the absorption by layers of skin, tissue and bones, and depends on the thickness, color and structure thereof. In the rest position, a further constant component emerges from the absorption of the blood in the veins. The pulsating component is caused by the arterial pulsation. The latter is created by the expansion and contraction of the arteries. Since the arterial blood volume change is measured indirectly in pulse oximetry, the second-changing part of the absorption signal is also referred to as photoplethysmogram (PPG).

In the clinical environment, the oxygen saturation in the arterial blood can be determined easily, non-invasively and relatively accurately with the aid of pulse oximetry. However, in the case of mobile application and active patients (e.g. infants), there are significant movement artifacts and so the oxygen saturation and heart rate can no longer be determined reliably. Movement artifacts in particular have a great influence on the reliability of pulse oximetry.

The origin of movement artifacts can be traced back to different physical processes. Firstly, the mechanical displacement of the sensor relative to the body (probe coupling) causes artifacts. However, these can be suppressed relatively well by mechanical fixing or by modeling the probe-coupling effect.

Secondly, physiological effects are also responsible for the artifacts. If venous pulsation occurs, the photoplethysmogram now no longer only describes the blood volume changes in the artery but also in the vein. It follows that there are errors in determining the oxygen saturation. By way of example, it is possible to determine that the movement artifacts are predominantly due to this venous pulsation and do not occur as much due to probe coupling.

The invention is based on the object of specifying a method, which is as precise as possible, for measuring the oxygen saturation of blood.

According to the invention, this object is achieved by a method with the features as per patent claim 1. Advantageous embodiments of the method according to the invention are specified in the dependent claims.

Accordingly, the invention provides for a method in which electromagnetic radiation having a first and a second wavelength is irradiated into the peripheral body part or irradiated through the peripheral body part, the reflected or transmitted radiation is measured to form two measurement signals, and the oxygen saturation of the blood is determined by evaluating the two measurement signals. In doing so, provision is made, in order to evaluate the two measurement signals, for use to be made of a mathematical mixing model, in which a useful-signal-related filter function related to the first wavelength, an interference-signal-related filter function related to the first wavelength, a useful-signal-related filter function related to the second wavelength, an interference-signal-related filter function related to the second wavelength, a useful source signal contained in the measurement signal and an interference source signal contained in the measurement signal are taken into account, and a statistical evaluation method is applied to the two measurement signals, wherein, as a boundary condition, the statistical independence of the useful source signal and the interference source signal is assumed and the useful source signal and the two useful-signal-related filter functions are determined with the aid of the evaluation method and the oxygen saturation of the blood is determined using the three aforementioned signals.

A significant advantage of the method according to the invention should be seen in the fact that it is very insensitive to movement influences, and so the measurement results remain very accurate even in the case of a certain amount of movement of the human or animal body while the measurement is taking place.

According to a preferred embodiment of the method, provision is made for the following mathematical mixing model to be used to evaluate the two measurement signals:

$$x_1(t) = h_{11}(t) * s_1(t) + h_{12}(t) * s_2(t)$$

$$x_2(t) = h_{21}(t) * s_1(t) + h_{22}(t) * s_2(t)$$

wherein $h_{11}(t)$ denotes the useful-signal-related filter function related to the first wavelength, $h_{12}(t)$ denotes the interference-signal-related filter function related to the first wavelength, $h_{21}(t)$ denotes the useful-signal-related filter function related to the second wavelength, $h_{22}(t)$ denotes the interference-signal-related filter function related to the second wavelength, $s_1(t)$ denotes the useful source signal contained in the measurement signal, $s_2(t)$ denotes the interference source signal contained in the measurement signal, $x_1(t)$ denotes the measurement signal at the first wavelength and $x_2(t)$ denotes the measurement signal at the second wavelength.

According to a particularly preferred embodiment of the method, provision is made for the oxygen saturation to be established using the three signals by virtue of the effective values of the two useful-signal-related filter functions being related to one another to form a ratio and the ratio being used to establish the oxygen saturation.

The oxygen saturation is preferably formed using the ratio by virtue of using the following determination formula:

$$SpO_2 = \frac{1 - k1 \cdot R}{k3 - k2 \cdot R}$$

where R denotes the ratio, k1 denotes a first constant, k2 denotes a second constant, k3 denotes a third constant and $SpO_2$ denotes the oxygen saturation value.

The first constant preferably lies in a range between 0.4 and 0.6, the second constant lies in a range between 0.3 and 0.4 and the third constant k3 lies in a range between 0.8 and 1.

According to a further particularly preferred embodiment of the method, provision is made not only for the oxygen saturation to be measured, but also for a photoplethysmographic signal to be additionally formed and displayed.

In respect of forming the photoplethysmographic signal, it is considered advantageous if one of the useful-signal-related filter functions is convoluted with the useful source signal to form a convolution signal and the photoplethysmographic signal is formed using the convolution signal.

The photoplethysmographic signal PPG(t) is preferably formed as per:

$$PPG(t) = h_{11} * s_1(t) \text{ or}$$

$$PPG(t) = h_{21} * s_1(t).$$

A measuring instrument for measuring the oxygen saturation of the blood flowing in a peripheral human or animal body part is also considered to be part of the invention.

According to the invention, provision is made in such a measuring instrument for an evaluation apparatus which applies a statistical evaluation method to the two measurement signals $x1(t)$ and $x2(t)$, wherein, as a boundary condition, the statistical independence of a useful source signal and an interference source signal is assumed. The useful source signal and useful-signal-related filter functions are determined with the aid of the evaluation method and the oxygen saturation of the blood is determined using the three aforementioned signals.

By way of example, the evaluation apparatus can be formed by data-processing equipment, which is programmed such that it can carry out the described method.

The measuring instrument preferably has a display apparatus for displaying the oxygen saturation and/or for displaying a photoplethysmographic signal.

The invention will be explained in more detail below on the basis of exemplary embodiments; here, in exemplary fashion.

For reasons of clarity, the same reference signs are used in the figures for identical or comparable objects.

The pump action of the heart in a human or animal body is manifested in a pulse wave, which, for example, can be measured in the form of a photoplethysmogram or photoplethysmographic signal—abbreviated PPG-signal or PPG(t) below. However, taking into account the physiological properties of the vessel system, a pulse wave measurable at the periphery, as a result of the branching of the arteries, additionally consists of a superposition of reflected waves which always occur when there is a significant change in the artery cross section.

Moreover, the flow properties within the arteries cause damping of high-frequency wave components, particularly in peripheral body parts such as the finger. Moreover, the properties of the vessel system change constantly. Thus, the body regulates the vasoconstriction of smooth muscles in order, for example, to match the blood pressure to the load conditions.

Nevertheless, the vessel system can be considered to be stationary for a brief period of time. At this moment, the vessel system acts like a filter, which filters the pressure signals of the heart contractions on the way to the measuring instrument. Possible interference, the origin of which for example lies in the movement and which is superposed on the measurement signal, is likewise filtered by the vessel system between the location of action and the finger.

Proceeding from these thoughts, a method will be explained below in an exemplary fashion, which is based on convolutive "independent component analysis" (ICA) and makes it possible to establish the source signals as such and hence the oxygen saturation as a result of statistical properties.

The method described below in exemplary fashion uses convolutive ICA for determining the oxygen saturation and for reconstructing the PPG signal.

In the following text, the method of "blind source separation", which can be used in the method, is initially presented. Here, the mixing models and, in an exemplary fashion, a method for separating signals on the basis of second-order statistics are explained.

Many areas of multi-channel biomedical signal acquisition are presented with the problem that the measured signals in fact represent a superposition of individual source signals. Methods of "blind source separation" make it possible to reconstruct the desired sources from the measured signals. The advantage thereof lies in the fact that only very little previous knowledge is required in respect of the sources themselves and the mixing thereof. A limitation for the separability lies in the statistical independence of the source signals; however, this can often be justified well on physical grounds. Algorithms that are based on these statistically independent components are therefore also called ICA (cf. documents [Köh05][HKO01] in the separate list of references).

Instantaneous linear superposition constitutes the simplest model for source signal mixing (cf. document [Bau05] in the separate list of references). Here, a linear combination of the source signals is measured in each case. These instantaneous values restrict the coefficients of the mixture to scalar factors.

Figure 1:
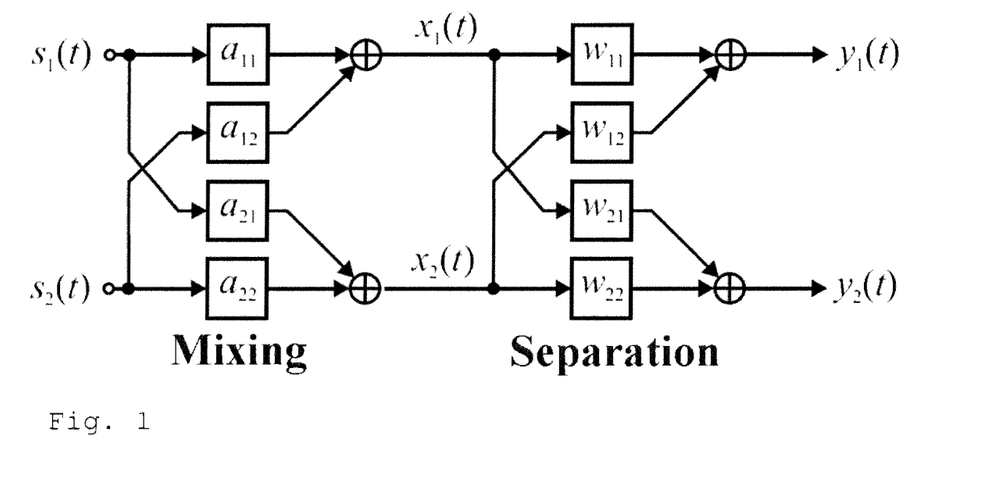
FIG. 1 shows a model for the instantaneous mixing and separation of two source and sensor signals.

FIG. 1 illustrates a model for instantaneous mixing and separation of two source and sensor signals. Mathematically, the superposition can be formulated as follows:

$$x_1(t)=a_{11}s_1(t)+a_{12}s_2(t) \tag{1.1}$$

$$x_2(t)=a_{21}s_1(t)+a_{22}s_2(t) \tag{1.2}$$

Here, $s_i(t)$ represent the source signals, $a_{ij}$ represent the mixing coefficients and $x_i$ represent the sensor signals. A compact representation is provided by the matrix form:

$$x(t)=A \cdot s(t) \tag{1.3}$$

The separation problem can be solved by applying the inverse matrix $W=A^{-1}$, as soon as A has a full rank. The separated signals y(t) then emerge as:

$$y(t)=W \cdot x(t) \tag{1.4}$$

If the mixing matrix can be determined exactly, the source signals can be reconstructed in ideal form, as can be seen in equation 1.5. Here I is the identity matrix.

$$y(t)=W \cdot As(t)=I \cdot s(t)=s(t) \tag{1.5}$$

Established ICA methods are based on different criteria of statistical independence. In the process, two random variables are denoted to be statistically independent if and only if the joint probability density function equals the product of the marginal distributions. Thus, the following applies:

$$p_x(x_1,x_2)=p_{x_1}(x_1) \cdot p_{x_2}(x_2) \tag{1.6}$$

ICA methods therefore merely evaluate statistical properties of the signals, as a result of which there are some limitations in the reconstruction of the source signals. Since every permutation P or scaling D of the output signals in turn supplies statistically independent signals in each case, the latter can also only be determined exactly up to these uncertainties (cf. document [Bau05]):

$$y(t)=PD \cdot s(t) \tag{1.7}$$

Figure 2:
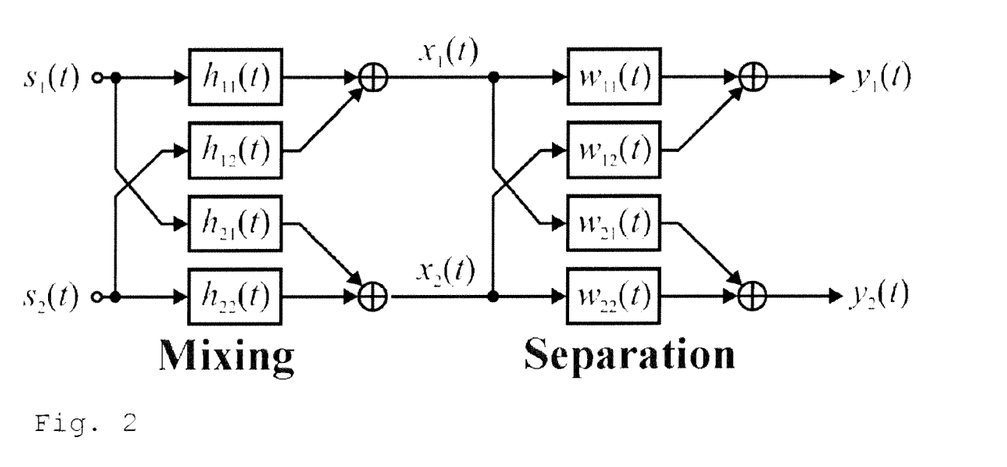
FIG. 2 shows a convolutive mixing and separating model and FIG. 3 shows an exemplary embodiment for a measuring instrument according to the invention, on the basis of which the method according to the invention is also once again explained in an exemplary fashion.

In contrast to the model of instantaneous linear superposition, the measured signals in the model of convolutive mixing emerge from a superposition of filtered source signals. With $h_{ij}(t)$ as impulse response from the mixing filters, the sensor signals emerge as:

$$x_1(t)=h_{11}(t)*s_1(t)+h_{12}(t)*s_2(t) \tag{1.8}$$

$$x_2(t)=h_{21}(t)*s_1(t)+h_{22}(t)*s_2(t) \tag{1.9}$$

Written in matrix form, A therefore no longer contains scalar values but rather impulse responses from the mixing filters:

$$x(t)=A*s(t) \tag{1.10}$$

FIG. 2 shows a convolutive mixing and separating model with the respective impulse responses $h_{ij}(t)$ and $w_{ij}(t)$.

If the mixture is formulated in frequency space, the convolution in equations 1.8 and 1.9 can be converted into a multiplication:

$$X_1(\omega,\tilde{t})=H_{11}(\omega) \cdot S_1(\omega,\tilde{t})+H_{12}(\omega) \cdot S_2(\omega,\tilde{t}) \tag{1.11}$$

$$X_2(\omega,\tilde{t})=H_{21}(\omega) \cdot S_1(\omega,\tilde{t})+H_{22}(\omega) \cdot S_2(\omega,\tilde{t}) \tag{1.12}$$

The matrix form is as follows:

$$X(\omega,\tilde{t})=A(\omega) \cdot S(\omega,\tilde{t}) \tag{1.13}$$

This procedure is made possible by applying the short-time Fourier transform STFT (cf. document [OSB04] in the attached list of references). In each frequency band, a complex-valued, instantaneous mixing problem is created, which can be solved using arbitrary methods from instantaneous ICA. These methods merely need to be expanded to complex-valued signals.

Since the mixing problem is solved independently in each frequency band, the sequence of some of the frequency bands may be interchanged, as a result of which a permutation correction becomes necessary. In order finally to reconstruct the time signals, the inverse short-time Fourier transform is preferably carried out as per document [OSB04] in the attached list of references.

In order to solve the mixing problem there is a row of established algorithms that deal with the analysis of statistical independence. They are based on different criteria and mainly rely upon statistical variables. If the source signals moreover have a temporal structure, it is expedient also to use correlations between time-offset signals for calculating the separation matrix (cf. document [Köh05] in the attached list of references).

For the purpose of suppressing artifacts in PPG signals, use can be made of such a method based on second-order statistics since the impulse-wave signal has great self-similarity and periodicity.

For better understanding, the following initially explains a method with instantaneous mixing; subsequently complex-valued signals are also considered, as a result of which it is also possible to separate convolutive mixtures.

In many ICA algorithms, so-called "sphering" or "prewhitening" is used in pre-processing. It serves to decorrelate and normalize the variances of the sensor signals to one. To this end, the sensor signals are transformed by means of a suitable sphering matrix M such that the whitened signals $x_s$ are finally decorrelated and the covariance matrix $C_{xs}$ thereof is also diagonal.

$$x_s=Mx=MAs \tag{1.14}$$

The sphering matrix M can be calculated by an eigenvalue decomposition of the covariance matrix $C_x=E[xx^T]$ of the mean-value-free signals x:

$$C_x=E[xx^T]=V\Lambda V^T \tag{1.15}$$

If V is the orthogonal matrix of eigenvectors and $\Lambda$ is the diagonal matrix with the associated eigenvalues of $C_x$, the sphering matrix M is given as inverse of the matrix root of $C_x$:

$$M = C_x^{-\frac{1}{2}} = \Lambda^{-\frac{1}{2}} V^T \tag{1.16}$$

The covariance of the transformed signals $x_s$ then have the structure of an identity matrix:

$$C_{x_s} = E[x_s x_s^T] = C_x^{-\frac{1}{2}} E[xx^T] C_x^{-\frac{1}{2}^T} = C_x^{-\frac{1}{2}} C_x C_x^{-\frac{1}{2}^T} = I \tag{1.17}$$

The prewhitening also ensures that the matrix O, to be found by the subsequent ICA stage, is orthogonal because the following holds true:

$$C_{x_s} = E[x_s x_s^T] = OE[ss^T]O^T = I, \text{ with } O = MA \quad (1.18)$$

The source signals $s_1(t)$ and $s_2(t)$ are statistically independent by definition, as a result of which, together with normalizing the variances to one, the covariance matrix of the source signals is also an identity matrix $$E[ss^T] = I, \quad (1.19)$$

and so it follows that $$OO^T = I \quad (1.20)$$

must also apply. Thus the mixing and separation matrix of the transformed data are likewise orthogonal and the search for the separation matrix is made significantly easier (cf. document [HKO01] in the list of references).

If the source signals have a temporal structure, it is expedient also to use correlations between time-offset signals for the separation. Preferably this is based on the uncorrelated property of the source signals s, as a result of which the cross-correlation thereof disappears for arbitrary time offsets $\tau$:

$$E[s_i(t)s_j(t+\tau)] = 0 \quad (1.21)$$

It is also possible to use spectral coloring of the respective signals, i.e. a self-similarity:

$$E[s_i(t)s_i(t+\tau)] \neq 0 \quad (1.22)$$

As a result of this, the covariance matrices $C_x(t, \tau)$ become diagonal at the times $\tau$:

$$C_s(t,\tau) = E[s(t)s^T(t+\tau)] = \Lambda(t,\tau) \quad (1.23)$$

Together with the model of instantaneous mixing from equation 1.3, this implies for the sensor signals that a set of covariance matrices $C_x(t, \tau)$ exists, for which all $\Lambda(t, \tau)$ are diagonal:

$$C_x(t,\tau) = E[x(t)x^T(t+\tau)] = E[As(t)(As(t+\tau))^T] = A\Lambda(t,\tau)A^T \quad (1.24)$$

Since the power of this method depends on the selection of suitable values for $\tau$, it is expedient to directly evaluate a whole set of covariance matrices. Moreover, as a result of prewhitening, the problem can be restricted to the search in the space of orthogonal matrices (cf. document [Köh05]). It is necessary to find an orthogonal matrix O which diagonalizes the set of covariance matrices $$C_{x_s}(t,\tau) = E[x_s(t)x_s^T(t+\tau)] = O\Lambda(t,\Lambda)O^T \quad (1.25)$$

for all considered times as follows (cf. document [Bau05]):

$$O^T C_{x_s}(t,\tau) O = \Lambda(t,\tau) \quad (1.26)$$

To this end, it is possible to use a joint diagonalization algorithm based on a Jacobi method. The method of joint diagonalization of a set of covariance matrices with time lag is also referred to as "second order blind identification" (SOBI) (cf. document BAMCM97]).

However, the goal of ideally diagonalizing the complete set of covariance matrices with time lag can almost never be achieved using real data. Nevertheless, it is possible to define a cost function J(O), which supplies a good approximation by a minimization (cf. document [HKO01]):

$$J(O) = \sum_{\tau \in S} \text{off}(O^T C_{x_s}(\tau) O) \quad (1.27)$$

The cost function J(O) adds all non-diagonal elements (off-operator) of the set S of covariance matrices and is minimized in the case of an optimal selection of the orthogonal matrix O, as a result of which the mixing matrix is also approximated well.

As already explained above, solving a convolutive mixing problem can be reduced to an instantaneous complex-valued ICA problem by applying the STFT. The SOBI method can be formulated analogously to equation 1.25 for complex-valued signals:

$$C_{x_s}(\omega,\tau) = E_t[X_s(\omega,\tilde{t})X_s^H(\omega,\tilde{t}+\tau)] = O(\omega)\Lambda(\omega,\tilde{t}+\tau)O(\omega)^H \quad (1.28)$$

Here too use can once again be made of joint diagonalization which together minimizes values of the off-diagonal matrix entries for a set of covariance matrices.

If a convolutive mixing problem is solved by means of a complex-valued instantaneous method such as SOBI, the established independent source signals per frequency band are available in unordered form (see equation 1.7). Therefore a permutation correction is required, which brings the pairs of unordered signals into a consistent order.

For the permutation correction, methods have been established which evaluate similarity measures between the permutated frequency bands or the consistency of the separation filters. By way of example, use can be made of a correlation-based method according to Rahbar and Reilly (cf. document [RR05]).

Starting point of the permutation correction are n signals per frequency band, separated by ICA, depending on the window shift $\tau$, which are represented in combined fashion as $Y_n(\omega, \tau)$.

A frequency band $w_k$ is used as a reference in order to permute a second band $w_j$ as correctly as possible. To this end, normalized correlations $\rho_{qp}$ of all possible pairs of q-th signal of the band k and p-th signal of the band j are calculated as follows:

$$\rho_{qp}(\omega_k, \omega_j) = \frac{\sum_{\tau} Y_q(\omega_k, \tau) Y_p(\omega_j, \tau)}{\sqrt{\sum_{\tau} Y_q^2(\omega_k, \tau)} \sqrt{\sum_{\tau} Y_p^2(\omega_j, \tau)}} \quad (1.29)$$

Subsequently, the sum of the normalized correlations $\rho_{qp}$ (P) of the involved signal pairs q and p is calculated for all possible permutations P. The best permutation is found when this similarity measure is maximal.

Figure 3:
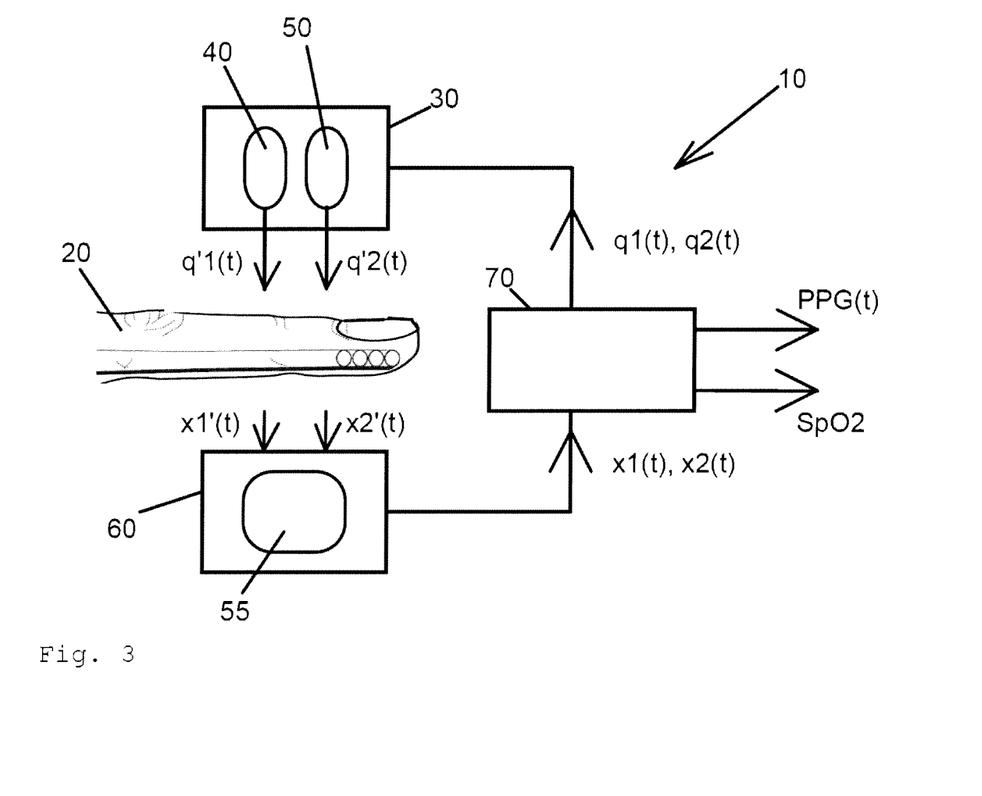

FIG. 3 shows an exemplary embodiment for a measuring instrument 10, which is suitable for measuring the oxygen saturation of the blood flowing in a peripheral human or animal body part 20 and can form a PPG signal. The measuring instrument 10 applies a convolutive ICA, which evaluates statistical properties for separating the source signals and uses the brief stationary property of the vessel system.

The measuring instrument 10 comprises a transmitter apparatus 30 with two light-emitting diodes 40 and 50 for generating electromagnetic radiation q1'(t) and q2'(t) having a first and a second wavelength; the two wavelengths are different. By way of example, the radiation q1'(t) is red light and the radiation q2'(t) is infrared light. By way of example, the two light-emitting diodes 40 and 50 are operated in a temporal multiplexing method.

A reception apparatus 60, having a photodetector 55, of the measuring instrument 10 is used to measure the transmitted radiation x1'(t) and x2'(t) irradiated through the peripheral body part 20, forming two measurement signals x1(t) and x2(t). The two measurement signals x1(t) and x2(t) reach an evaluation apparatus 70 of the measuring instrument 10. The evaluation apparatus 70 evaluates the two measurement signals and measures the oxygen saturation of the blood forming an oxygen saturation value SpO2. Moreover, it forms a PPG signal PPG(t).

The PPG signal PPG(t) mirrors the superposition of various peripheral pressure waves and pressure waves moving in the direction of the heart, which, for example, is expressed in the two-peaked nature of the signal measured at the finger. Here, there is strong positive superposition of the peripherally traveling wave with a wave reflected at the pre-capillary resistance vessels of the abdomen. High-frequency components of the pressure wave emanating from the heart are damped as a result of the elasticity of the blood vessels and the flow properties accompanying this.

Such a superposition can be considered to be a convolutive mixture; the corresponding model is illustrated in FIG. 2. The useful source signal $s_1(t)$ corresponds to the pressure wave emanating from the pump action of the heart, while movement artifacts are caused by the second interference source signal $s_2(t)$. Reflections and damping of the higher-frequency components are implemented in this model as filtering by the impulse responses $h_{11}(t)$ and $h_{21}(t)$ for the pressure wave and $h_{12}(t)$ and $h_{22}(t)$ for the artifacts. Therefore the convolutive ICA can be used well for separating these two signal components.

However, the properties of the vessel system can only be considered to be stationary for a brief period of time because the regulation of the cardiovascular system continuously adapts the vessel width and elasticity. The evaluation apparatus 70 therefore preferably decomposes the continuous signal in relatively short sections for which the statistically independent components are respectively determined. The optimum compromise between good separability and stationarity in this case is an interval of preferably between 5 and 15 seconds, for example approximately 10 seconds (e.g. 10.24 s). The temporal split is preferably brought about by means of the windowed overlap-add decomposition (cf. document [PM07]) into blocks with a length of e.g. n=512 and an overlap of e.g. $n_{Overlap}$=256 sampled values. A Bartlett window is preferably used as window function.

Since PPG signals have a pronounced periodicity and self-similarity, these properties are preferably particularly taken into account when selecting a suitable ICA method. The evaluation apparatus 70 will therefore preferably use the SOBI algorithm since the latter explicitly uses this self-similarity in order to separate the independent sources. Since the convolutive ICA is carried out in frequency space, an STFT method (STFT: short-time Fourier transform) is used to divide the time signals in blocks of e.g. respectively $n_{FFT}$=32 sampled values with an overlap of e.g. $n_{Overlap}$=24 sampled values in e.g. 17 frequency bands.

A prewhitening step carried out by the evaluation apparatus 70 preferably decorrelates the sensor signals and normalizes the variances to e.g. one, as a result of which the search for the mixing matrix in the SOBI method is restricted to orthogonal matrices and hence it is simplified. Overall, the joint diagonalization for example diagonalizes 50 time-offset covariance matrixes, as a result of which adequate capabilities for the method are achieved in order to determine the mixing matrix A.

As a result of the orthogonality, the separation matrix W can also be calculated easily by the evaluation apparatus 70 from the mixing matrix A determined by means of ICA. After separation, the pairs of independent source signals are available unordered in each frequency band, as a result of which a permutation correction becomes necessary. To this end, use is made of a method based on the correlation. Determining the best possible permutation P of the source signals finally also renders possible the correction of the established mixing and separation matrices to $A_f$ and $W_f$, as a result of which it is possible to reconstruct the time signal using ISTFT (ISTFT: inverse short-time Fourier transform). However, for each processed block of e.g. 512 sampled values, the two reconstructed time signals are in turn available in unordered form. Thus, at this time it is still unclear which of the separated signals is a PPG and which is an artifact source. The measure of entropy H(X) was found in trials to be an appropriate means for fixing the order:

$$H(X) = -\sum_{\forall i} P(x_i) ld(P(x_i)) \quad (1.30)$$

Here, the PPG signal has higher entropy than the interference signal, which makes a unique assignment possible. The continuous source signals are subsequently reconstructed in the evaluation apparatus 70 by means of overlap-add synthesis.

In the convolutive mixing model, the signals, subject to interference and established by the measuring system, for the red and infrared wavelengths when formulated in the frequency space respectively correspond to the signals $X_1(w, \tilde{t})$ and $X_2(w, \tilde{t})$ (equations 1.31 and 1.32).

$$X_1(\omega,\tilde{t}) = H_{11}(\omega) \cdot S_1(\omega,\tilde{t}) + H_{12}(\omega) \cdot S_2(\omega,\tilde{t}) \quad (1.31)$$

$$X_2(\omega,\tilde{t}) = H_{21}(\omega) \cdot S_1(\omega,\tilde{t}) + H_{22}(\omega) \cdot S_2(\omega,\tilde{t}) \quad (1.32)$$

If $S_1(w, \tilde{t})$ is the original PPG signal in the mixing model, then $S_2(w, \tilde{t})$ represents either the artifact source or, in the case without movement, a noise process. $H_{11}(w)$ thus comprises a complex-valued factor for each frequency band, said factor representing a measure for the component of the PPG source signal $S_1(w, \tilde{t})$ in the measured red signal $X_1(w, \tilde{t})$, while $H_{21}(w)$ quantifies the complex-valued factor for the component in the infrared signal $X_2(w, \tilde{t})$.

In principle, the ratio R, i.e. the quotient of the normalized intensities for both wavelengths, is evaluated when calculating the oxygen saturation. However, only signal components caused by the pulsation of the artery should be included in the intensity signals. In the convolutive mixing model assumed here, this ratio is present separately for each frequency band by virtue of the coefficients of the mixing filter $H_{11}(w)$ and $H_{21}(w)$. In order to increase the robustness, the evaluation apparatus 70 will therefore preferably use RMS averaging over the values of the coefficients in order to determine R:

$$R \approx \frac{\text{RMS}(|H_{11}|)}{\text{RMS}(|H_{21}|)} = \frac{\sqrt{\sum_{\forall i} |H_{11}(\omega_i)|^2}}{\sqrt{\sum_{\forall i} |H_{21}(\omega_i)|^2}} \quad (1.33)$$

The following equation with linear extrapolation under 70% is preferably used as determination formula for the oxygen saturation:

$$SpO_2 = \frac{1 - 0.55 \cdot R}{0.9 - 0.35 \cdot R} \qquad (1.34)$$

In conjunction with the figures, the method for measuring the oxygen saturation was described in an exemplary fashion for the case where electromagnetic radiation is irradiated through the peripheral body part and the transmitted radiation is measured and evaluated. Additionally, or as an alternative thereto, it is possible to measure and evaluate the reflected radiation.

LIST OF REFERENCES

[BAMCM97] Belouchrani, A.; Abed-Meraim, K.; Cardoso, J. F.; Moulines, E.: A blind source separation technique using second-order statistics. In: IEEE Transactions on Signal Processing 45 (1997), no. 2, pp. 434-444

[Bau05] Baumann, W.: Optimierung frequenzvarianter Nullbeamformer für akustische Signale mittels Statistik höoherer Ordnung—Anwendungen im Kfz und in Büroräumen [Optimizing frequency-variant zero-beam former for acoustic signals by means of higher-order statistics—applications in motor vehicles and office space], Technische Universitit Berlin, Diss., 2005

[Bro00] Bronzino, J. D. (ed.): The Biomedical Engineering Handbook. CRC/Taylor & Francis, 2000, Chapter 86.1

[HKO01] Hyvärinen, A.; Karhunen, J.; Oja, E.: Independent Component Analysis. New York: John Wiley & Sons, 2001

[Köh05] Köhler, Bert-Uwe: Konzepte der statistischen Signalverarbeitung [Concepts of statistical signal processing]. Springer Berlin Heidelberg New York, 2005

[OSB04] Oppenheim, Alan V.; Schafer, Ronald W.; Buck, John R.: Zeitdiskrete Signalverarbeitung [Time-discrete signal processing]. Pearson Studium, 2004

[PMO7] Proakis, John G.; Manolakis, Dimitris G.: Digital Signal Processing—Principles, Algorithms and Applications. Pearson Education, 2007

[RR05] Rahbar, K.; Reilly, J. P.: A Frequency Domain Method for Blind Source Separation of Convolutive Audio Mixtures. In: IEEE Transactions on Speech and Audio Processing 13 (2005), no. 5, pp. 832-844

LIST OF REFERENCE SIGNS

10 Measuring instrument
20 Body part
30 Transmitter apparatus
40 Light-emitting diode
50 Light-emitting diode
55 Photodetector
60 Reception apparatus
70 Evaluation apparatus
PPG(t) PPG signal
SpO2 Oxygen saturation value

The invention claimed is:

1. A method for measuring the oxygen saturation of the blood flowing in a peripheral human or animal body part, in which electromagnetic radiation ($q1'(t)$, $q2'(t)$) having a first wavelength and a second wavelength is irradiated into the peripheral body part or irradiated through the peripheral body part, reflected or transmitted radiation ($x1'(t)$, $x2'(t)$) corresponding to the first wavelength and the second wavelength is measured to form two measurement signals ($x1(t)$, $x2(t)$), and the oxygen saturation of the blood is determined by evaluating the two measurement signals, comprising:

evaluating the two measurement signals with a mathematical mixing model, in which a useful-signal-related filter function related to the first wavelength, an interference-signal-related filter function related to the first wavelength, a useful-signal-related filter function related to the second wavelength, an interference-signal-related filter function related to the second wavelength, a useful source signal contained in the measurement signals and an interference source signal contained in the measurement signals are used in the evaluation, applying a statistical evaluation method to the two measurement signals, wherein, as a boundary condition, the statistical independence of the useful source signal and the interference source signal is assumed and determining therefrom the useful source signal and the two useful-signal-related filter functions, and determining the oxygen saturation of the blood using the three signals determined with the statistical evaluation, wherein the mathematical mixing model is a convolutive mixing model where the two measurement signals emerge from a superposition of filtered source signals which are filtered by mixing filters, wherein the following mathematical mixing model is used in evaluating the two measurement signals:

$$x_1(t) = h_{11}(t) * s_1(t) + h_{12}(t) * s_2(t)$$

$$x_2(t) = h_{21}(t) * s_1(t) + h_{22}(t) * s_2(t)$$

wherein $h_{11}(t)$ denotes the useful-signal-related filter function related to the first wavelength, $h_{12}(t)$ denotes the interference-signal-related filter function related to the first wavelength, $h_{21}(t)$ denotes the useful-signal-related filter function related to the second wavelength, $h_{22}(t)$ denotes the interference-signal-related filter function related to the second wavelength, $s_1(t)$ denotes the useful source signal contained in the measurement signal, $s_2(t)$ denotes the interference source signal contained in the measurement signal, $x_1(t)$ denotes the measurement signal at the first wavelength and $x_2(t)$ denotes the measurement signal at the second wavelength.

2. The method as claimed in claim 1,
wherein the oxygen saturation is established using the three signals with the effective values of the two useful-signal-related filter functions being related to one another to form a ratio and the ratio being used to establish the oxygen saturation.

3. The method as claimed in claim 2,
wherein the oxygen saturation is formed using the ratio according to the following determination formula:

$$SpO_2 = \frac{1 - k1 \cdot R}{k3 - k2 \cdot R}$$

where R denotes the ratio, k1 denotes a first constant, k2 denotes a second constant, k3 denotes a third constant and $SpO_2$ denotes the oxygen saturation value.

4. The method as claimed in claim 3,
wherein the first constant lies in a range between 0.4 and 0.6, the second constant lies in a range between 0.3 and 0.4 and the third constant lies in a range between 0.8 and 1.

5. The method as claimed in claim 1,
wherein a photoplethysmographic signal is additionally formed and displayed.

6. The method as claimed in claim 5,
wherein one of the useful-signal-related filter functions is convoluted with the useful source signal to form a convolution signal and wherein the photoplethysmographic signal is formed using the convolution signal.

7. The method as claimed in claim 6,
wherein the photoplethysmographic signal PPG(t) is formed according to the following formulae:

$$PPG(t) = h_{11} * s_1(t) \text{ or}$$

$$PPG(t) = h_{21} * s_1(t).$$

8. A measuring instrument for measuring the oxygen saturation of the blood flowing in a peripheral human or animal body part, comprising a transmitter apparatus for generating electromagnetic radiation having a first and a second wavelength, a reception apparatus for measuring the transmitted radiation irradiated through the peripheral body part or the radiation reflected by the peripheral body part for the purpose of forming two measurement signals (x1(t), x2(t)), and an evaluation apparatus for evaluating the two measurement signals and for determining the oxygen saturation of the blood, wherein
the evaluation apparatus is configured to:
evaluate the two measurement signals with a mathematical mixing model, in which mathematical mixing model a useful-signal-related filter function related to the first wavelength, an interference-signal-related filter function related to the first wavelength, a useful-signal-related filter function related to the second wavelength, an interference-signal-related filter function related to the second wavelength, a useful source signal contained in the measurement signals and an interference source signal contained in the measurement signals are taken into account,
apply a statistical evaluation to the two measurement signals, wherein, as a boundary condition, the statistical independence of the useful source signal and the interference source signal is assumed and the useful source signal and the two useful-signal-related filter functions are determined as a result of applying the statistical evaluation and
determine the oxygen saturation of the blood using the three signals determined with the statistical evaluation,
wherein the mathematical mixing model is a convolutive mixing model where the two measurement signals emerge from a superposition of filtered source signals which are filtered by mixing filters,
wherein the evaluation apparatus uses the following mathematical mixing model to evaluate the two measurement signals:

$$x_1(t) = h_{11}(t) * s_1(t) + h_{12}(t) * s_2(t)$$

$$x_2(t) = h_{21}(t) * s_1(t) + h_{22}(t) * s_2(t)$$

wherein $h_{11}(t)$ denotes the useful-signal-related filter function related to the first wavelength, $h_{12}(t)$ denotes the interference-signal-related filter function related to the first wavelength, $h_{21}(t)$ denotes the useful-signal-related filter function related to the second wavelength, $h_{22}(t)$ denotes the interference-signal-related filter function related to the second wavelength, $s_1(t)$ denotes the useful source signal contained in the measurement signal, $s_2(t)$ denotes the interference source signal contained in the measurement signal, $x_1(t)$ denotes the measurement signal at the first wavelength and $x_2(t)$ denotes the measurement signal at the second wavelength.

\* \* \* \* \*